(12) United States Patent
Otsuka (10) Patent No.: US 12,256,896 B2
(45) Date of Patent: Mar. 25, 2025

(54) ENDOSCOPE DISTAL END FRAME AND ENDOSCOPE

(71) Applicant: OLYMPUS CORPORATION, Hachioji (JP)

(72) Inventor: Masaki Otsuka, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 381 days.

(21) Appl. No.: 17/735,262

(22) Filed: May 3, 2022

(65) Prior Publication Data
US 2022/0257094 A1 Aug. 18, 2022

Related U.S. Application Data

(63) Continuation of application No. PCT/JP2021/001514, filed on Jan. 18, 2021.

(30) Foreign Application Priority Data

Jan. 30, 2020 (JP) .................. 2020-013746

(51) Int. Cl.
*A61B 1/00* (2006.01)
*A61B 1/018* (2006.01)
*A61B 1/06* (2006.01)

(52) U.S. Cl.
CPC ........ *A61B 1/00137* (2013.01); *A61B 1/0008* (2013.01); *A61B 1/00096* (2013.01); *A61B 1/00165* (2013.01); *A61B 1/0676* (2013.01)

(58) Field of Classification Search
CPC .............. A61B 1/00137; A61B 1/0008; A61B 1/00096; A61B 1/00165; A61B 1/0676; A61B 1/018; A61B 1/0125
See application file for complete search history.

(56) References Cited

U.S. PATENT DOCUMENTS

| 5,725,477 A | * | 3/1998 | Yasui ................. A61B 1/00091 600/125 |
| 2007/0249907 A1 | * | 10/2007 | Boulais ................ A61B 1/0676 600/179 |
| 2012/0209072 A1 | * | 8/2012 | Oue .................... A61B 1/00091 600/129 |

(Continued)

FOREIGN PATENT DOCUMENTS

| JP | S5854805 U1 | 4/1983 |
| JP | H09105871 A | 4/1997 |

(Continued)

OTHER PUBLICATIONS

English Translation of an International Search Report (ISR) dated Apr. 6, 2021, issued in International Application No. PCT/JP2021/001514.

*Primary Examiner* — Anh Tuan T Nguyen
*Assistant Examiner* — Rynae E Boler
(74) *Attorney, Agent, or Firm* — Holtz, Holtz & Volek PC (57) ABSTRACT

An endoscope distal end frame includes: a holder including a first through hole, the holder being a primary molding made of a colored resin; and a distal end part including a second through hole that is concentric with the first through hole, the distal end part being a secondary molding made of a transparent resin layered on the holder. The first through hole has a diameter larger than a diameter of the second through hole.

6 Claims, 12 Drawing Sheets

(56) References Cited

U.S. PATENT DOCUMENTS

| | | | |
|---|---|---|---|
| 2013/0274554 A1 | 10/2013 | Sato | |
| 2017/0245734 A1* | 8/2017 | Kaneko | ............... A61B 1/307 |
| 2020/0046205 A1* | 2/2020 | Ueda | ............... A61B 1/0051 |

FOREIGN PATENT DOCUMENTS

| | | | |
|---|---|---|---|
| JP | 2004261408 A | 9/2004 | |
| JP | 2005131902 A | 5/2005 | |
| JP | 2012024545 A | 2/2012 | |
| JP | 2016055103 A | 4/2016 | |
| WO | 2013054753 A1 | 4/2013 | |
| WO | 2014064401 A1 | 5/2014 | |

* cited by examiner

ENDOSCOPE DISTAL END FRAME AND ENDOSCOPE

This application is a continuation of PCT International Application No. PCT/JP2021/001514 filed on Jan. 18, 2021 which claims the benefit of priority from Japanese Patent Application No. 2020-013746 filed on Jan. 30, 2020, the entire contents of which are incorporated herein by reference.

BACKGROUND

The present disclosure relates to an endoscope distal end frame and an endoscope.

In recent years, double moldings are often used in electric products for the purpose of reducing assembling costs and increasing aesthetic appeal. There is however a difference in temperature between a primary molding and a secondary molding that is molded by ejecting a secondary molding material to the primary molding, which is the difference associated with a difference between the times of ejection, and therefore welding of the surface of the primary molding because of ejection of the secondary molding material is sometimes insufficient.

To deal with such a problem, for example, Japanese Laid-open Patent Publication No. 2005-1391902 discloses a method of setting a molten resin temperature of a primary molding material at a high temperature and thus extremely thinning a skin layer of the surface of a primary molding, thereby increasing a weld strength between the primary molding and a secondary molding.

SUMMARY

According to one aspect of the present disclosure, there is provided an endoscope distal end frame including: a holder including a first through hole, the holder being a primary molding made of a colored resin; and a distal end part including a second through hole that is concentric with the first through hole, the distal end part being a secondary molding made of a transparent resin layered on the holder, wherein the first through hole has a diameter larger than a diameter of the second through hole.

The above and other features, advantages and technical and industrial significance of this disclosure will be better understood by reading the following detailed description of presently preferred embodiments of the disclosure, when considered in connection with the accompanying drawings.

DETAILED DESCRIPTION

An embodiment of an endoscope distal end frame and an endoscope system including the endoscope distal end frame according to the disclosure will be described below with reference to the accompanying drawings. The disclosure is not limited to the following embodiment and components in the following embodiment include those easily replaceable by those skilled in the art or those substantially same.

Figure 1:
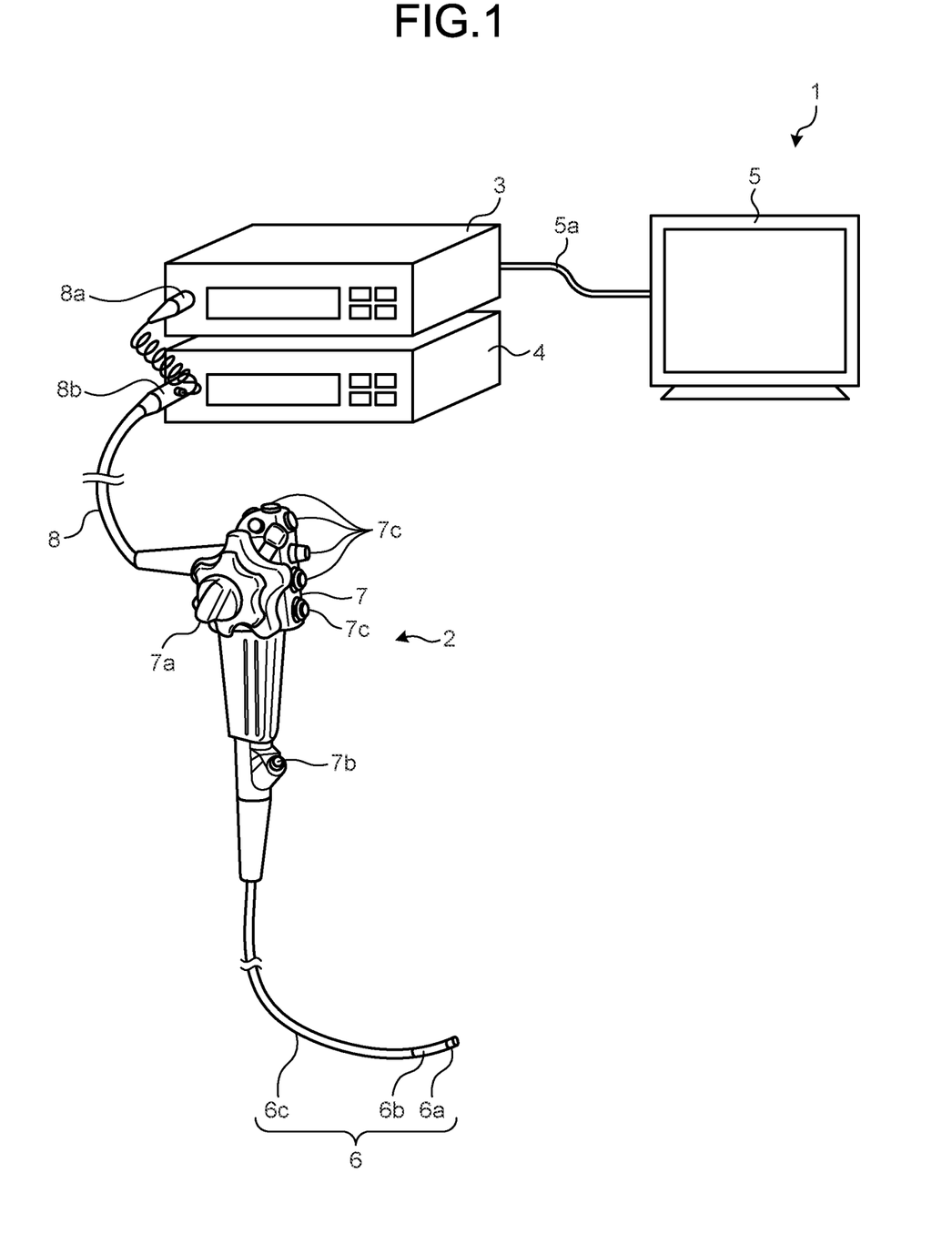
FIG. 1 is a diagram schematically illustrating an overall configuration of an endoscope system according to an embodiment.

FIG. 1 is a diagram schematically illustrating an overall configuration of an endoscope system 1 according to an embodiment. As illustrated in FIG. 1, the endoscope system 1 according to the embodiment includes an endoscope 2 that captures an in-vivo image of a subject and generates an in-vivo image signal of the subject, an information processing device 3 that performs given image processing on the image signal captured by the endoscope 2 and controls each unit of the endoscope system 1, a light source device 4 that generates illumination light of the endoscope 2, and a display device 5 that displays an image of the image signal after the image processing performed by the information processing device 3.

The endoscope 2 includes an insertion unit 6 that is inserted into the subject, an operation unit 7 that is on the side of a proximal end part of the insertion unit 6 and that is held by a practitioner, and a universal cord 8 that is flexible and that extends from the operation unit 7.

The insertion unit 6 is enabled using a light guide consisting of an illumination fiber, an electronic cable, an optical fiber, or the like. The insertion unit 6 includes a distal end part 6a incorporating an imaging device, a curve part 6b that includes a curving pipe to be described below and that flexibly curves, and a flexible tube 6c that is flexible and that is arranged on the side of a proximal end part of the curve part 6b. In the distal end part 6a, an illuminator that illuminates the inside of the subject via an illumination lens, an observation unit that captures an in-vivo image of the subject, and an opening that communicates a treatment tool channel are arranged.

The operation unit 7 includes a curve knob 7a that causes the curve part 6b to curve in up and down directions and left and right directions, a treatment tool insertion unit 7b through which a treatment tool, such as a biological forceps or a laser scalpel, is inserted into a body cavity of the subject, and a plurality of switch parts 7c for operating peripherals, such as the information processing device 3, the light source device 4, an air transmission device, a water transmission device, a gas transmission device and the curving pipe. The treatment tool that is inserted from the treatment tool insertion unit 7b comes out of the opening at the distal end of the insertion unit 6 via the treatment tool channel that is provided inside.

The universal cord 8 is configured using a light guide consisting of an illumination fiber, a cable, or the like. The universal cord 8 bifurcates at the proximal end and the end of one of the branches is a connector 8a and the proximal end of the other branch is a connector 8b. The connector 8a is detachable from the connector of the information processing device 3. The connector 8b is detachable from the light source device 4. The universal cord 8 transmits illumination light that is emitted from the light source device 4 to the distal end part 6a via the connector 8b and the light guide consisting of the illumination fiber. The universal cord 8 transmits the signal of the image that is captured by the imaging device to be described below to the information processing device 3 via the cable and the connector 8a.

The information processing device 3 performs the given image processing on the image signal that is output from the connector 8a and controls the entire endoscope system 1.

The light source device 4 is configured using a light source that emits light, a condenser lens, etc. Under the control of the information processing device 3, the light source device 4 emits light from the light source and supplies the light as the illumination light to the inside of the subject that is a subject to the endoscope 2 to which the light source device 4 is connected via the connector 8b and the light guide consisting of the illumination fiber of the universal cord 8.

The display device 5 is configured using a display using liquid crystals or organic electro luminescence (EL). The display device 5 displays various types of information containing the image on which the given image processing has been performed by the information processing device 3 via a video cable 5a. This allows the practitioner to operate the endoscope 2 while looking at the image (in-vivo image) that is displayed by the display device 5 and accordingly observe a desired position in the subject and determine symptoms.

Figure 2:
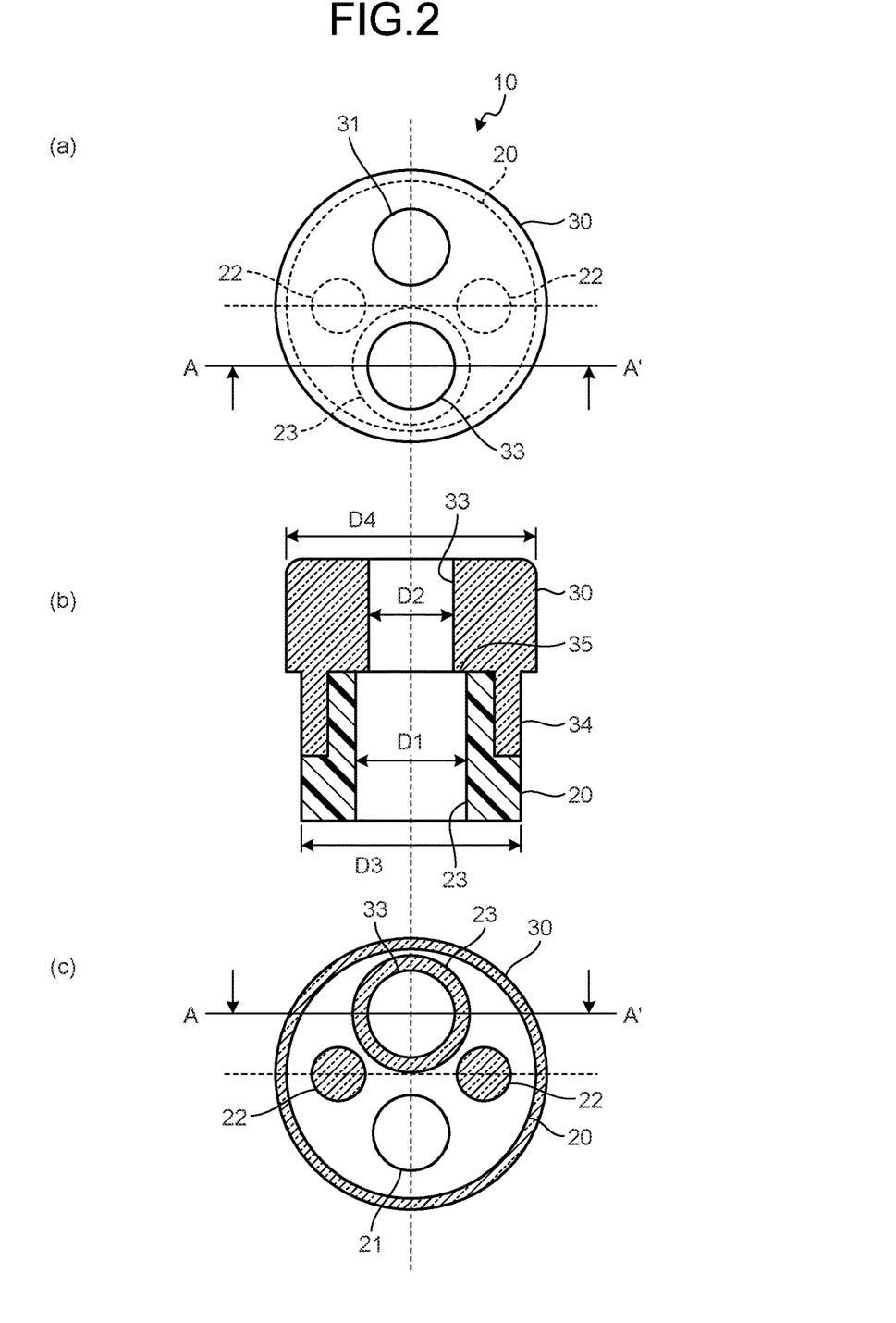
FIG. 2 illustrates an endoscope distal end frame that is used in the endoscope system in FIG. 1. (a) is a front view of the endoscope distal end frame, (b) is a cross-sectional view of the endoscope distal end frame taken along the A-A' line in (a), and (c) is a back view of the endoscope distal end frame.

A configuration of an endoscope distal end frame 10 that is arranged in the distal end part 6a of the endoscope 2 will be described with reference to the accompanying drawings. In FIG. 2, (a) is a front view of the endoscope distal end frame 10 that is used in the endoscope system 1 in FIG. 1, (b) is a cross-sectional view of the endoscope distal end frame 10 taken along the A-A' line in (a), and (c) is a back view of the endoscope distal end frame 10.

The endoscope distal end frame 10 includes a holder 20 that is a primary molding that is molded from a colored resin and a distal end part 30 that is a secondary molding that is molded from a transparent resin. The distal end part 30 is layered on the holder 20.

As illustrated in (c) of FIG. 2, the holder 20 includes through holes 21, 22 and 23. The through hole 21 holds the observation unit, the through hole 22 hold the illuminator, and the through hole 23 holds a channel tube for a treatment tool channel. The holder 20 is formed of the colored resin to prevent illumination light that is emitted by the illuminator from straying. The through hole 23 herein functions as a first through hole.

As illustrated in (a) of FIG. 2, the distal end part 30 includes though-holes 31 and 33. In the distal end part 30, no through hole is formed in positions corresponding to the through holes 22 that hold the illuminator. The distal end part 30 is formed of the transparent resin that transmits light that is emitted from the illuminator. The light that is emitted from the illuminator to the subject and reflected is incident on the observation unit via the through hole 31. The through hole 33 herein functions as a second through hole. The through hole 23 and the through hole 33 are a treatment tool channel into which a treatment tool is inserted.

In the endoscope distal end frame 10, the through hole 23 and the through hole 33 are in concentric circles and are formed such that a diameter D1 of the through hole 23 is larger than a diameter D2 of the through hole 33. The larger diameter D1 of the through hole 23 than the diameter D1 of the through hole 33 makes it possible to effectively prevent separation at a resin interface between the through hole 23 and the through hole 33. On the other hand, the through hole 21 and the through hole 31 are formed in equal diameters and in concentric circles in consideration of ensurance of incidence of reflected light on the observation unit, and a joint strength at a resin interface between the through hole 21 and the through hole 31 may be increased by setting the diameter of the through hole 21 at a diameter larger than the diameter of the through hole 31.

The distal end part 30 includes a cover part 34 that covers an outer circumference of the holder 20. The cover part 34 covers the whole outer circumference of the holder 20 on a side of the distal end. Alternatively, the cover part 34 may cover part of the outer circumference on the side of the distal end. The cover part 34 and the outer circumference of the holder 20 are flush. Because of provision of the cover part 34, the resin interface of the endoscope distal end frame 10 on the side of the outer circumference is in a position different from the position of a parting line and accordingly a shear stress applied to the resin interface on the side of the outer circumference at the separation reduces, which makes it possible to prevent separation at the resin interface. Furthermore the area of joint between the holder 20 and the distal end part 30 increases and accordingly the joint strength increases. Furthermore, the holder 20 is formed such that its outer diameter D3 is smaller than an outer diameter D4 of the distal end part 30. Setting the outer diameter D3 of the holder 20 at a diameter smaller than the outer diameter D4 of the distal end part 30 makes it possible to reduce unevenness of the outer shape when an exterior member is attached to the outer circumference of the holder 20 and the cover part 34.

Figure 3:
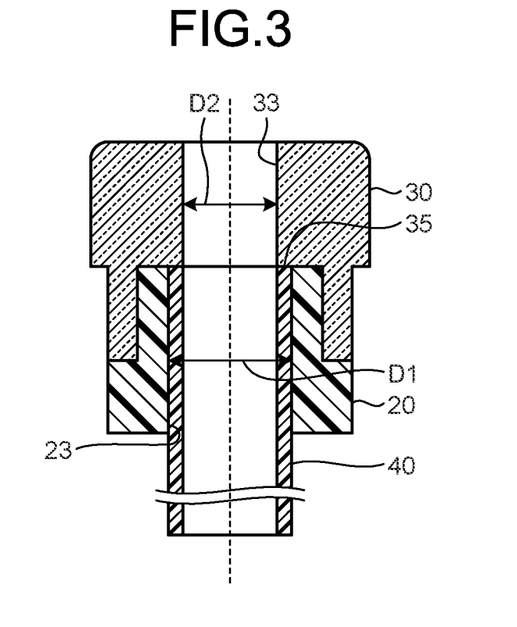
FIG. 3 is a cross-sectional view of the endoscope distal end frame in FIG. 2 with a channel tube being attached thereto.

FIG. 3 is a cross-sectional view of the endoscope distal end frame 10 in FIG. 2 with a channel tube 40 attached thereto. In the through hole 23 and the through hole 33 that constitute the treatment tool channel, the diameter D1 of the through hole 23 is larger than the diameter D2 of the through hole 33. A step 35 is formed between the through hole 23 and the through hole 33. The step 35 functions as a surface on which the channel tube 40 abuts. The treatment tool is inserted into the channel tube 40. In order to insert the treatment tool easily, it is preferable that the width of the step 35 ((D1−D2)/2) be approximately equal to a thickness of the channel tube.

Figure 4:
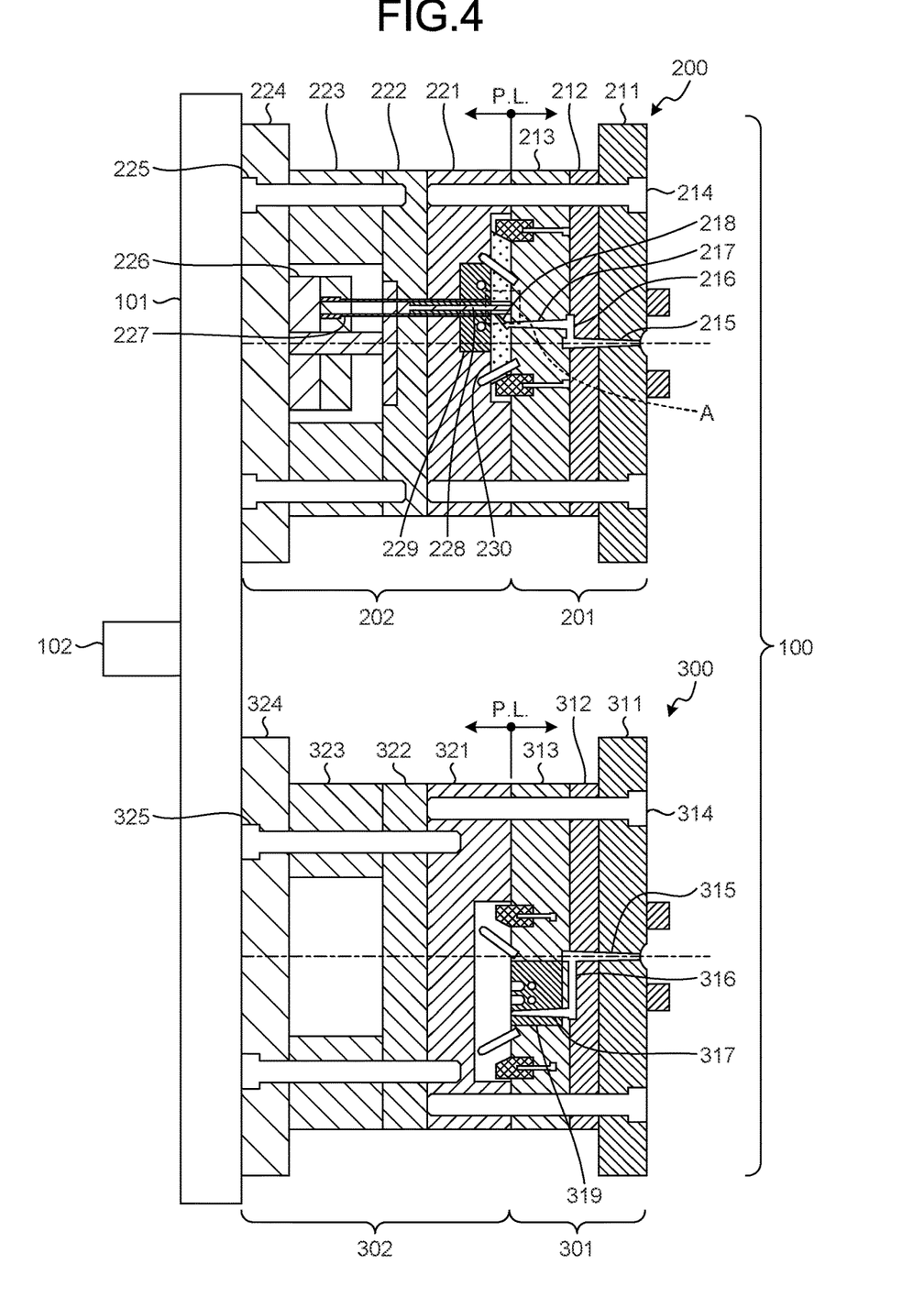
FIG. 4 is a cross-sectional view illustrating a configuration of a double molding die that molds the endoscope distal end frame in FIG. 2 and is a diagram illustrating a mold clamping state before filling of a primary molding cavity with a primary molding resin.

A double molding die 100 for manufacturing the endoscope distal end frame 10 will be described with reference to the accompanying drawings. FIG. 4 is a cross-sectional view illustrating a configuration of the double molding die 100 that molds the endoscope distal end frame 10 in FIG. 2. FIG. 4 illustrates a mold clamping state of the double molding die 100.

The double molding die 100 is attached to a double molding machine not illustrated in the drawing according to the positions of a primary injection nozzle and a secondary injection nozzle. The double molding die 100 includes a primary molding die 200 and a secondary molding die 300. The primary molding die 200 includes a fixed primary molding die 201 and a movable molding die 202 that is arranged against the fixed primary molding die 201 with a parting line ("P.L." below) in between. The secondary molding die 300 includes a fixed secondary molding die 301 and a movable dummy molding die 302 that is arranged against the fixed secondary molding die 301 with the P.L. in between.

The movable molding die 202 and the movable dummy molding die 302 are supported by a movable platen 101 and are configured movably in open and close directions with respect to the fixed primary molding die 201 and the fixed secondary molding die 301. The movable molding die 202 and the movable dummy molding die 302 are configured such that rotation of the movable platen 101 on a rotation shaft 102 enables changes of the respective positions of the movable molding die 202 and the movable dummy molding die 302. In other words, because of rotation of the movable platen 101 on the rotation shaft 102 by 180 degrees, the movable molding die 202 moves from a position opposed to the fixed primary molding die 201 to a position opposed to the fixed secondary molding die 301 and the movable dummy molding die 302 moves from the position opposed to the fixed secondary molding die 301 to a position opposed to the fixed primary molding die 201.

The fixed primary molding die 201 mainly includes an attachment plate 211, a fall plate 212, a fixed primary side mold plate 213 and a plurality of guide pins 214. In the fixed primary molding die 201, a primary sprue 215, a runner 216, a secondary sprue 217 and a gate 218 are formed.

The movable molding die 202 mainly includes a movable side mold plate 221, a receiving plate 222, a spacer block 223, an attachment plate 224, a plurality of fastening bolts 225, a rejector plate 226, an ejector pin 227, and a core pin 228. The movable side mold plate 221 is provided with a primary slide insert 230 via a movable insert 229 on a surface opposed to the fixed primary side mold plate 213 and a receding part 230a is formed on a side on which the primary slide insert 230 is opposed to the fixed primary side mold plate 213. The receding part 230a forms a primary molding cavity 220.

The core pin 228 is arranged in the receding part 230a of the primary slide insert 230 and forms the primary molding cavity 220 that is cylindrical. The core pin 228 is incorporated in the receiving plate 222 such that the core pin 228 keeps a relative position to the movable side mold plate 221 through a process of molding a double molding (primary molding process and a secondary molding process).

The fixed secondary molding die 301 mainly includes an attachment plate 311, a fall plate 312, a fixed secondary side mold plate 313, and a plurality of guide pins 314. In the fixed secondary molding die 301, a primary sprue 315, a runner 316, a secondary sprue 317, and a gate 318 are formed. The fixed secondary side mold plate 313 is provided with a secondary fixed insert 319 on a surface opposed to the movable dummy molding die 302 and a receding part 319a is formed on a side on which the secondary fixed insert 319 is opposed to the movable dummy molding die 302. A boss part 319b is arranged in the receding part 319a of the secondary fixed insert 319 and the receding part 319a forms a secondary molding cavity 320 (see FIG. 11) that is cylindrical.

The movable dummy molding die 302 mainly includes a movable dummy side mold plate 321, a receiving plate 322, a spacer block 323, an attachment plate 324 and a plurality of fastening bolts 325.

A method of manufacturing an endoscope distal end frame using the double molding die 100 will be described below with reference to FIGS. 5 to 9. In the method of manufacturing an endoscope distal end frame that is a double molding, the primary molding process and the secondary molding process are performed.

Primary Molding Process

Figure 5:
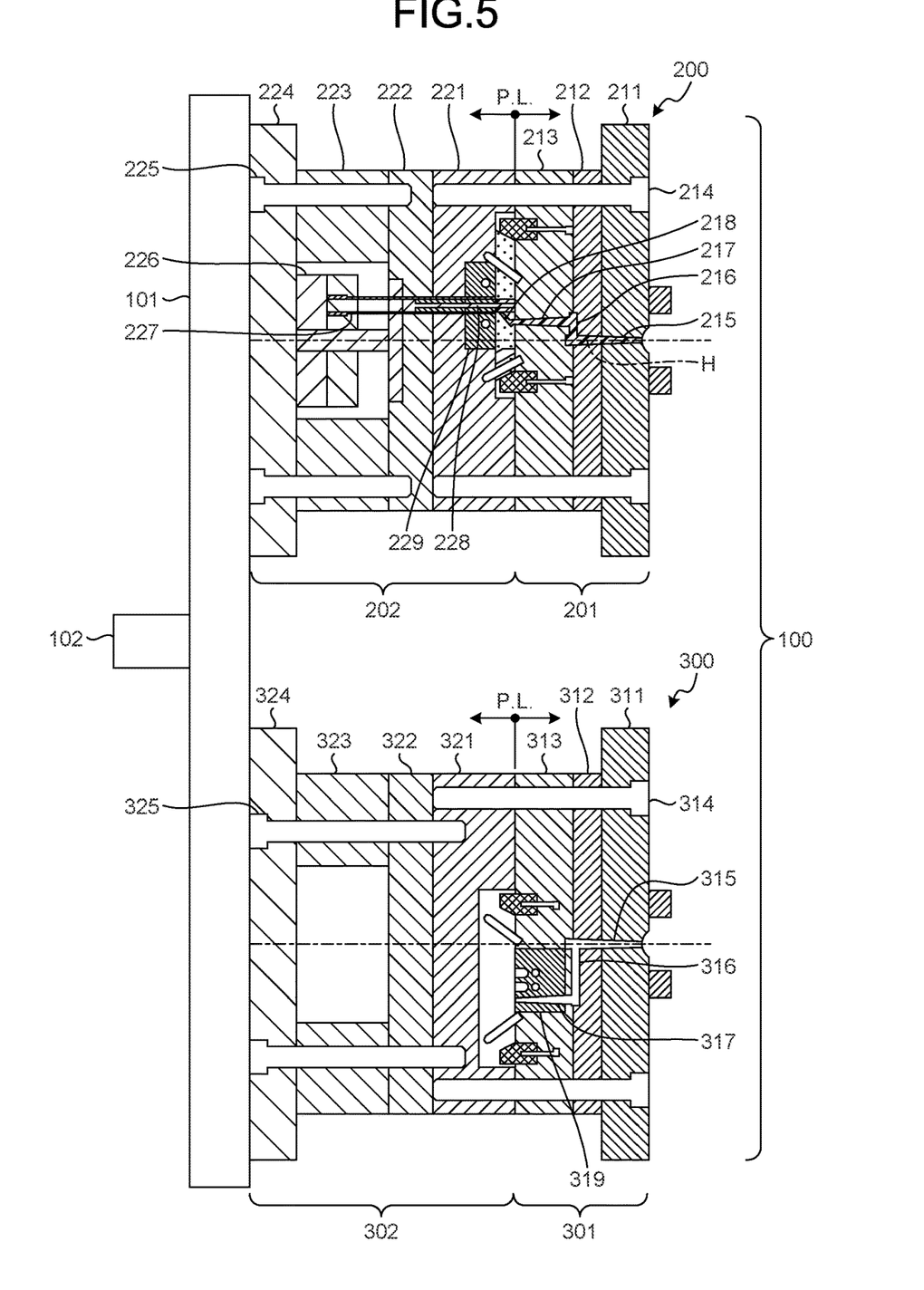
FIG. 5 is a cross-sectional view illustrating a state in which the primary molding cavity of the double molding die in FIG. 4 is filled with the primary molding resin.
Figure 6:
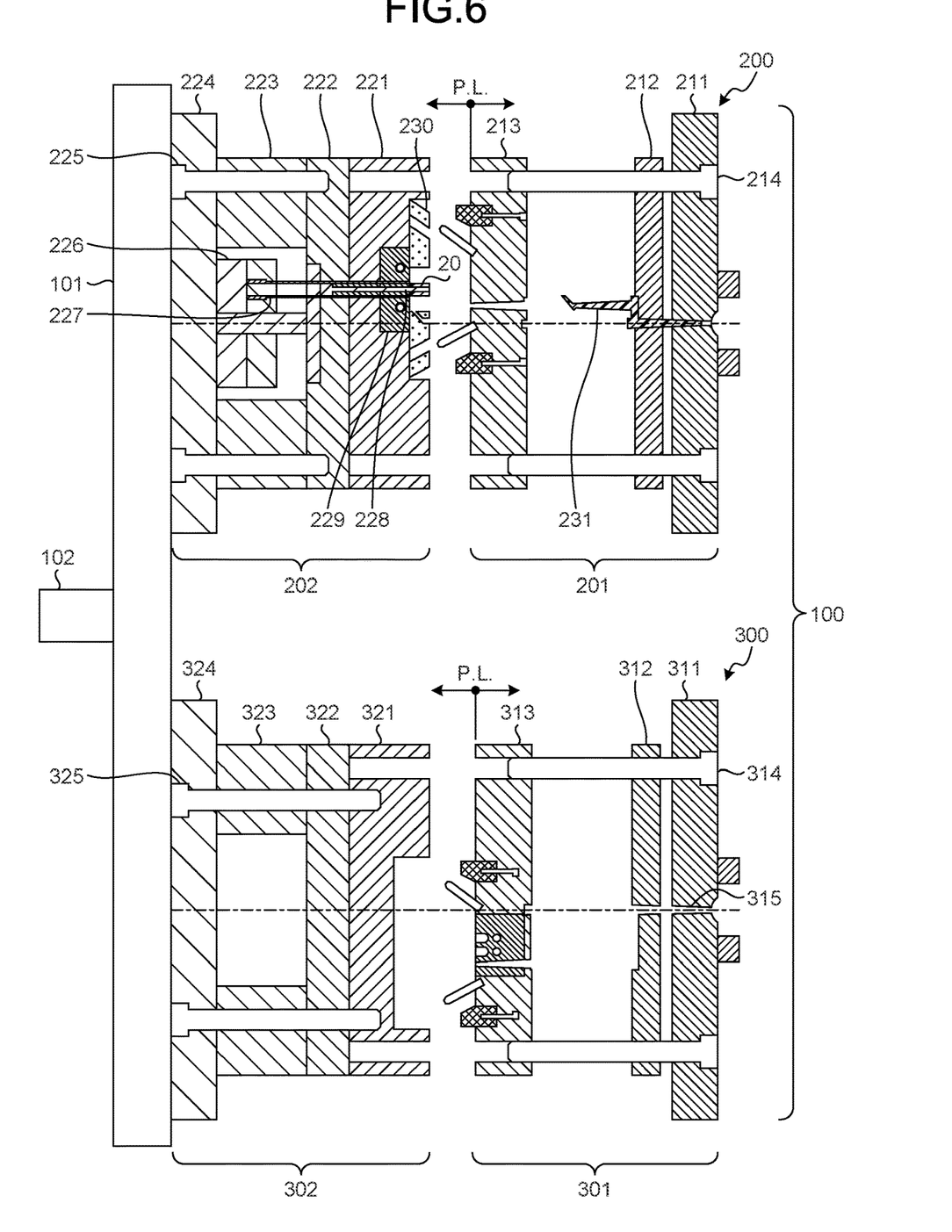
FIG. 6 is a cross-sectional view illustrating a state of mold opening of the double molding die in FIG. 5 at the time of mold opening.

First of all, as illustrated in FIG. 5, with the double molding die 100 being clamped, the primary molding cavity 220 that is formed by the fixed primary side mold plate 213, the ejector pin 227, the core pin 228, the movable insert 229, and the primary slide insert 230 is filled with a colored primary molding resin r1 via the primary sprue 215, the runner 216, the secondary sprue 217 and the gate 218 of the fixed primary molding die 201. For example, a colored resin obtained by, for example, coloring polycarbonate (PC) with an opaque color is usable as the primary molding resin r1. Details of the primary molding cavity 220 will be described below (see FIG. 10).

subsequently, as illustrated in FIG. 6, the double molding die 100 is opened. Thus, the primary molding resin r1 with which the primary molding cavity 220 is filled is separated into the holder 20 that is the primary molding that is held by the core pin 228 of the movable molding die 202 and a primary molding runner 231 that is held by the fixed primary molding die 201. The holder 20 that is separated from the fixed primary molding die 201 is formed in a shape of a cylinder with a through hole.

Figure 7:
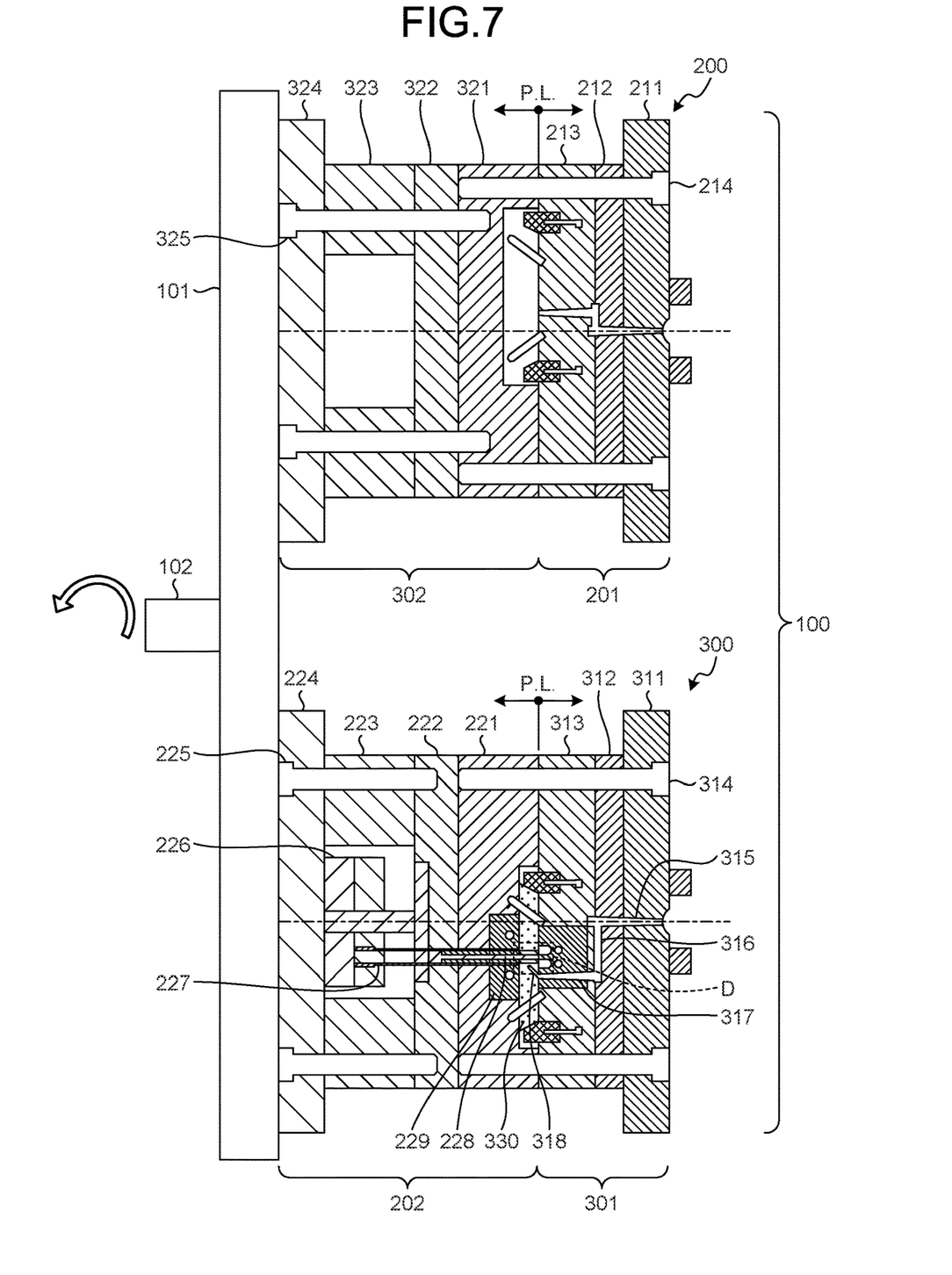
FIG. 7 is a cross-sectional view illustrating a state in which the double molding die in FIG. 6 is moved to a side of a secondary molding die and is clamped.

Subsequently, as illustrated in FIG. 7, after the positions of the movable molding die 202 holding the holder 20 with the core pin 228 and the movable dummy molding die 302 are switched by rotating the movable platen 101 on the rotation shaft 102 by 180 degrees, mold clamping is performed. Note that, in order to simplify the illustration in the drawing, a secondary slide insert 330 is illustrated in place of the primary slide insert 230 that is attached to the movable side mold plate 221. Accordingly, the secondary molding cavity 320 is formed between the receding part 319a of the secondary fixed insert 319 and the holder 20 and the secondary slide insert 330. Details of the secondary molding cavity 320 will be described in detail below (see FIG. 11).

Secondary Molding Process

Figure 8:
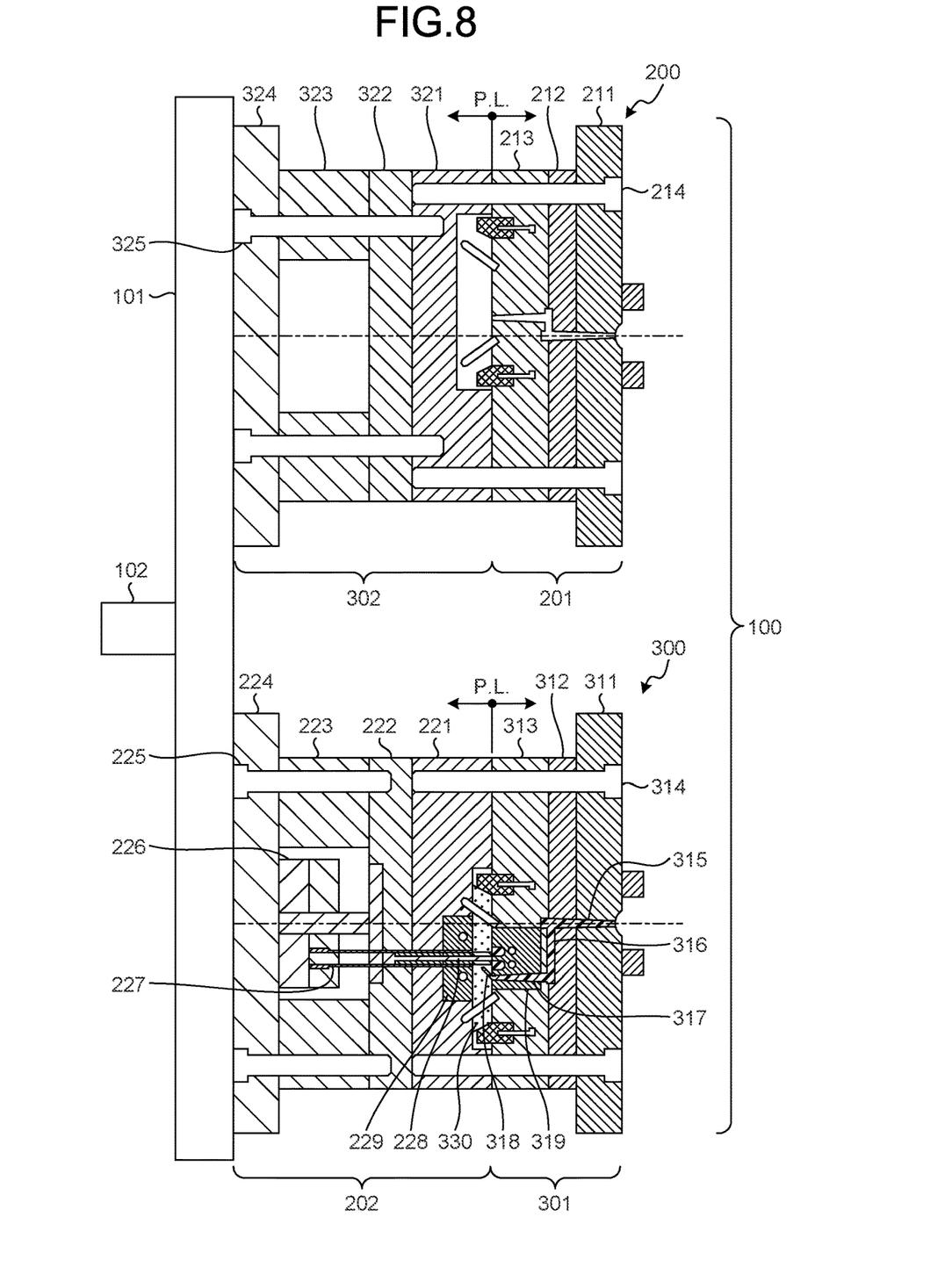
FIG. 8 is a cross-sectional view illustrating a state in which a secondary molding cavity of the double molding die in FIG. 7 is filled with a secondary molding resin.

Subsequently, as illustrated in FIG. 8, with the double molding die 100 being clamped, the secondary molding cavity 320 is filled with a transparent secondary molding resin r2 via the primary sprue 315, the runner 316, the secondary sprue 317, and the gate 318 of the fixed secondary molding die 301. For example, a transparent resin, such as polycarbonate (PC), is usable as the secondary molding resin r2.

Figure 9:
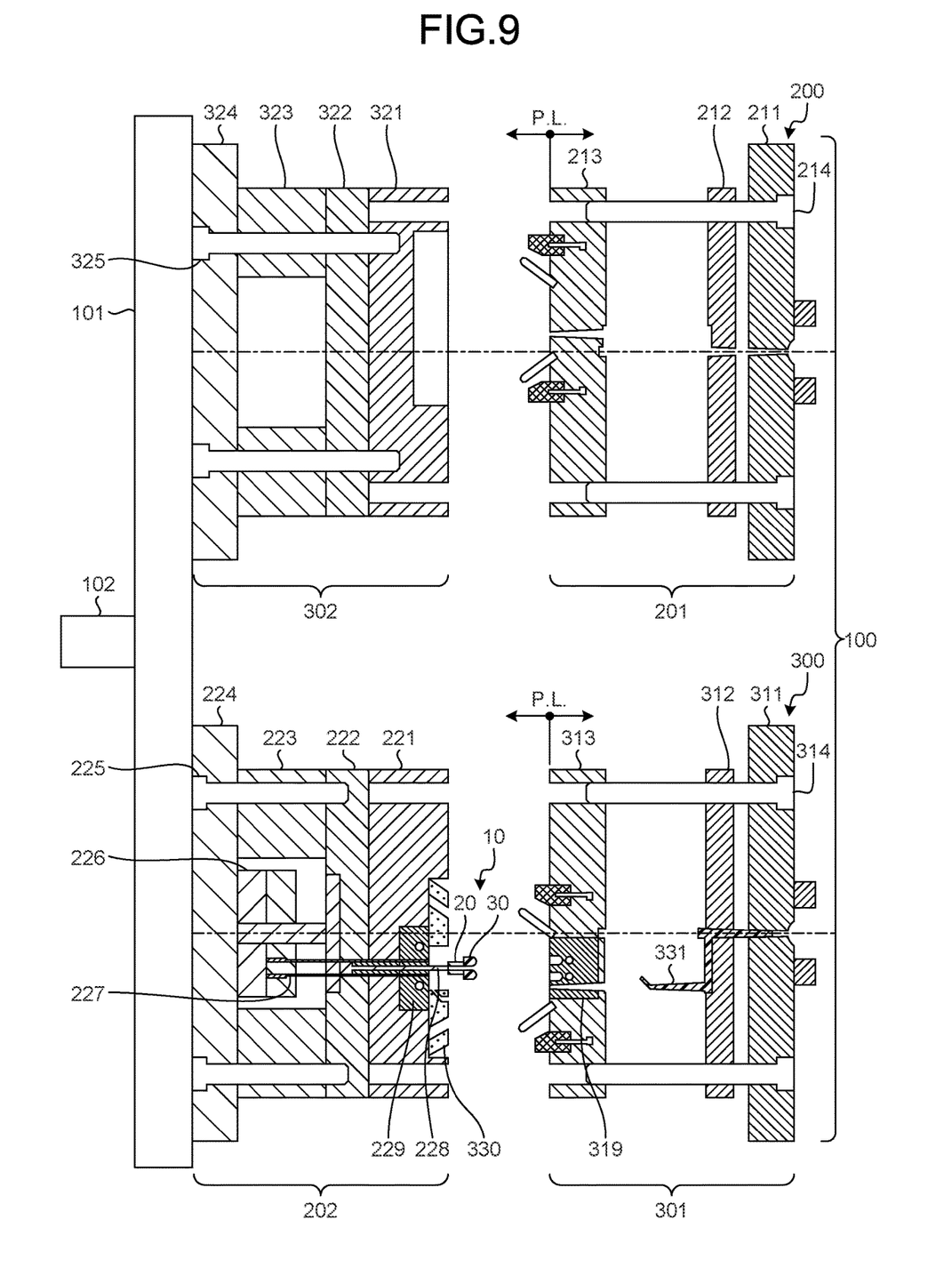
FIG. 9 is a cross-sectional view illustrating a state in which, after the double molding die in FIG. 8 is opened, the double molding is separated from the molding die.

Subsequently, as illustrated in FIG. 9, the double molding die 100 is opened. Thus, the secondary molding resin r2 with which the secondary molding cavity 320 is filled is separated into the endoscope distal end frame 10, which consists of the holder 20 that is the primary molding held by the core pin 228 of the movable molding die 202 and the distal end part 30 that is the secondary molding, and a secondary molding runner 331 that is held by the fixed secondary molding die 301.

The rejector plate 226 moves in a P.L. direction and accordingly the endoscope distal end frame 10, which is held by the core pin 228 of the movable molding die 202, is pushed by the ejector pin 227 and thus is separated from the movable molding die 202. The distal end part 30 that is separated from the movable molding die 202 is formed transparently to have a through hole.

The primary molding cavity 220 and the secondary molding cavity 320 that are formed in the double molding die 100 and the endoscope distal end frame 10 that is manufactured by the above-described manufacturing method will be described below with reference to FIGS. 10 to 14.

Primary Molding Cavity

Figure 10:
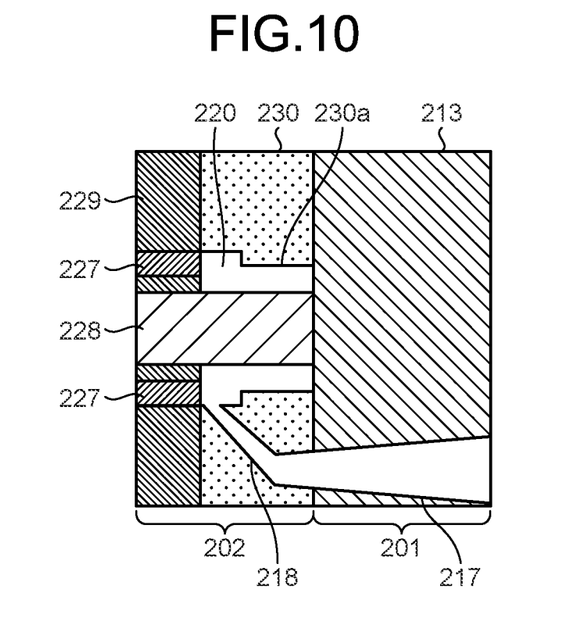
FIG. 10 is a cross-sectional view illustrating the primary molding cavity that is formed in the double molding die and is an enlarged view of the part A in FIG. 4.

FIG. 10 is an enlarged view of the part A in FIG. 4 and illustrates a cross-sectional shape of the primary molding cavity 220 at the time of mold clamping in the primary molding process. The primary molding cavity 220 is formed by the receding part 230a of the primary slide insert 230, the fixed primary side mold plate 213, the ejector pin 227, and the core pin 228. A distal end surface of the core pin 228 is in contact with the fixed primary side mold plate 213 and an end face of the primary molding cavity 220 on the side of the P.L. and the distal end surface of the core pin 228 are flush. Accordingly, the shape of the holder 20 with the through hole in the direction in which the molding die is opened is defined.

The receding part 230a is formed into a cylindrical shape with a given diameter and the receding part 230a and the gate 218 that is a port from which the primary molding resin r1 flows in communicate. A step for providing the cover part 34 is formed around the receding part 230a.

Secondary Molding Cavity

Figure 11:
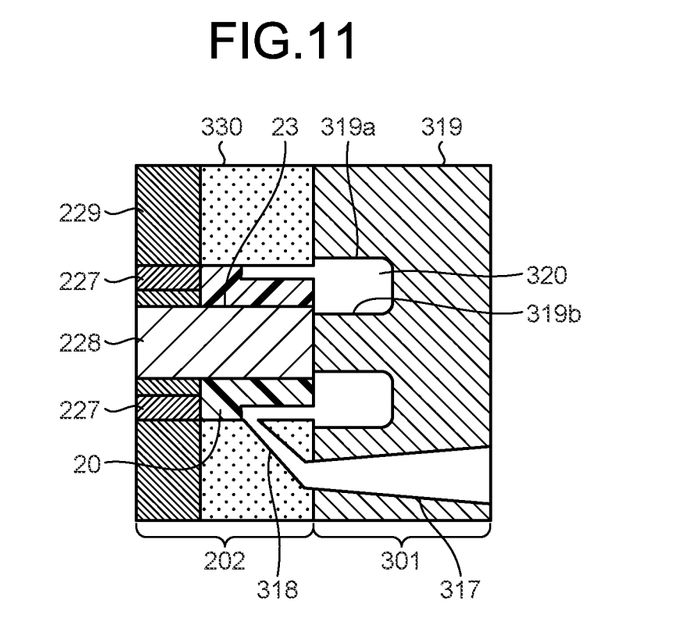
FIG. 11 is a cross-sectional view illustrating the secondary molding cavity that is formed in the double molding die and is an enlarged view of the part D in FIG. 7.

FIG. 11 is an enlarged view of the part D in FIG. 7 and illustrates a cross-sectional shape of the secondary molding cavity 320 at the time of mold clamping in the secondary molding process. The secondary molding cavity 320 is formed by a primary molding separation surface, the secondary slide insert 330, the core pin 228, and the receding part 319a of the secondary fixed insert 319.

The holder 20 includes the through hole 23 and the core pin 228 is inserted into the center of the through hole 23. The entire distal end surface of the boss part 319b that is arranged in the receding part 319a of the secondary fixed insert 319 and the distal end surface of the core pin 228 are in contact with each other. The boss part 319b forms the through hole 33 of the distal end part 30. In the embodiment, the diameter of the boss part 319b is smaller than the diameter of the core pin 228.

Figure 12A:
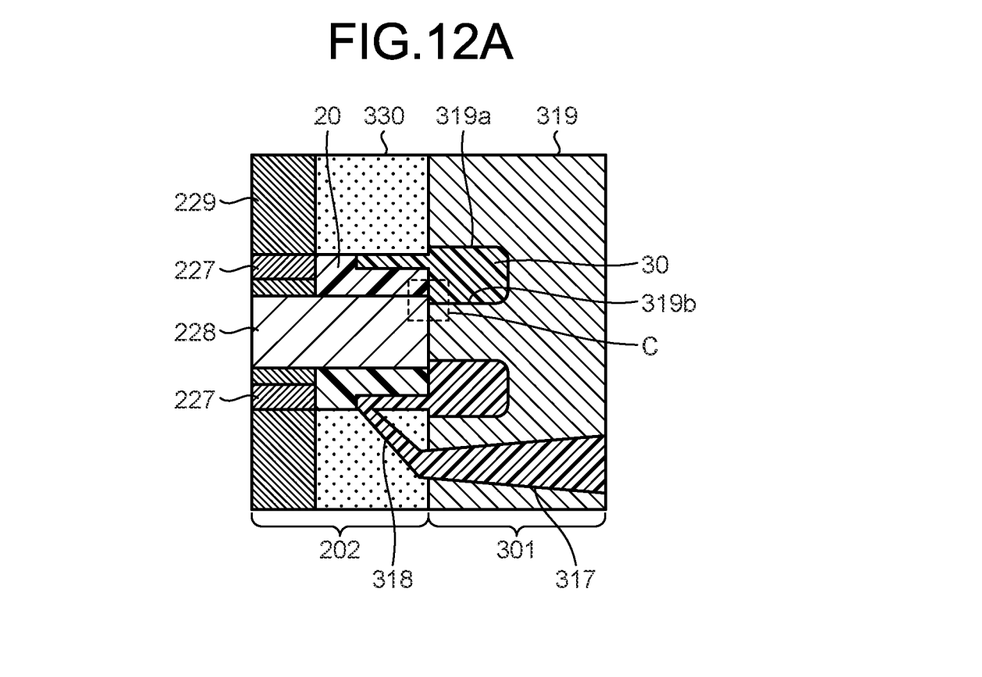
FIG. 12A is a cross-sectional view of the double molding die with the secondary molding cavity being filled with the secondary molding resin and FIG. 12B is an enlarged view of the part C in FIG. 12A.
Figure 12B:
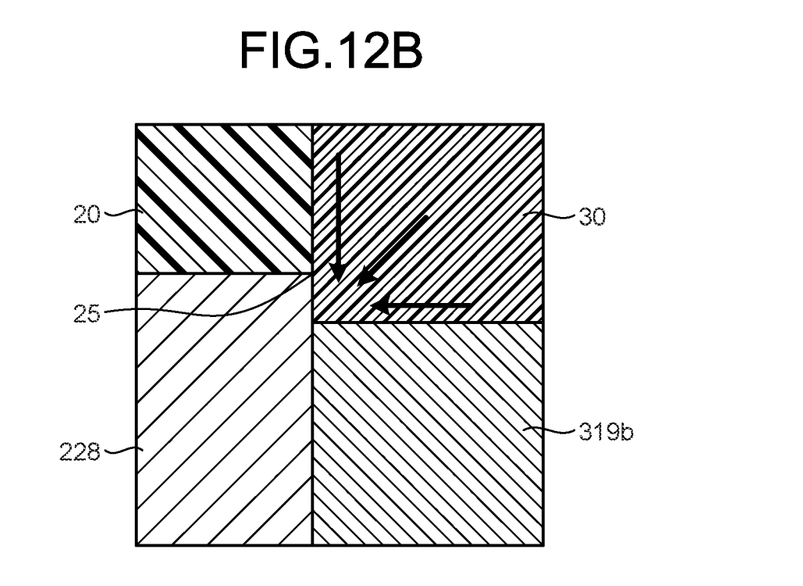

FIGS. 12A and 12B are diagrams of the double molding die 100 with its secondary molding cavity 320 being filled with the secondary molding resin r2. The secondary molding resin r2 is supplied to the space between the secondary slide insert 330 and the holder 20 from the gate 318. As illustrated in FIGS. 12A and 12B, the secondary molding resin r2 flows above the holder 20 and passes above an end 25 of the primary and secondary molding resin interface in the through hole and the periphery of the part of contact between the boss part 319b and the core pin 228 is filled with the secondary molding resin r2. In the embodiment, because the molten secondary molding resin r2 passes above the end 25 of the primary and secondary molding resin interface, the molten secondary molding resin r2 flows also at the end 25 of the primary and secondary molding resin interface. Accordingly, because the surface of the holder 20 near the end 25 of the primary and secondary molding resin interface is caused to be molten again and is sufficiently welded with the distal end part 30 that is the secondary molding, it is possible to inhibit separation of the primary molding resin r1 and the secondary molding resin r2 at the primary and secondary molding resin interface due to a tensile force of the outer circumferential surface of the boss part 319b on the inner surface of the through hole of the distal end part 30 in the mold opening direction (boss part separation resistance) and it is possible to enable the endoscope distal end frame 10 to have high quality of appearance without molding failure.

Figure 13:
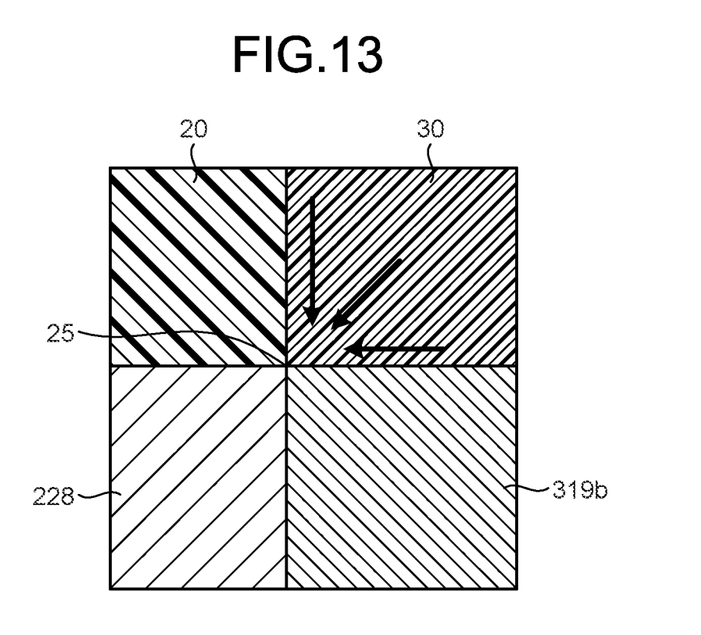
FIG. 13 is an enlarged cross-sectional view of a known double molding die with a secondary molding cavity being filled with a secondary molding resin.
Figure 14:
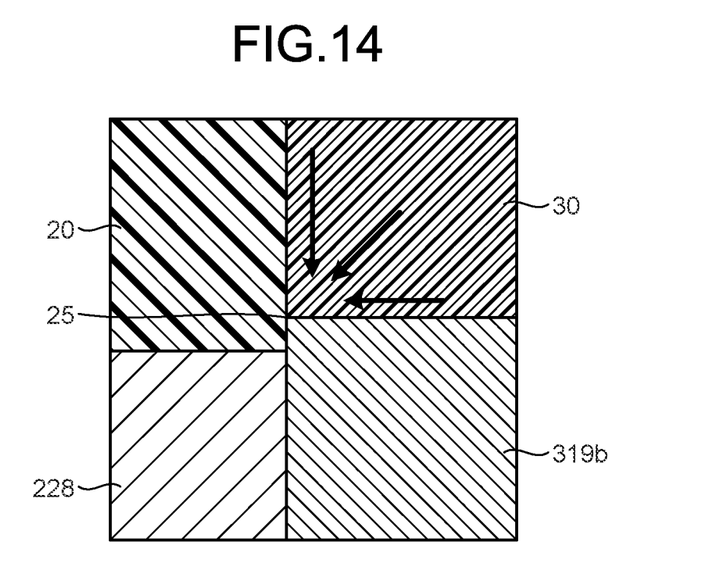
FIG. 14 is an enlarged cross-sectional view of a known double molding die with a secondary molding cavity being filled with a secondary molding resin.

On the other hand, FIG. 13 and FIG. 14 are enlarged cross-sectional views of a known double molding die with the secondary molding cavity 320 being filled with the secondary molding resin. FIG. 13 illustrates the case where the diameters of the through holes of the holder 20 and the distal end part 30 are the same and FIG. 14 illustrates the case where the diameter of the through hole of the holder 20 is smaller than the diameter of the through hole of the distal end part 30. In the cases illustrated in FIG. 13 and FIG. 14, because the end 25 of the primary and secondary molding resin interface is the terminal of filling with the secondary molding resin r2, the surface of the holder 20 is less likely to be molten again in the end 25 of the primary and secondary molding resin interface and the holder 20 and the distal end part 30 are not welded sufficiently. In such a case, separation of the primary molding resin r1 and the secondary molding resin r2 at the primary and secondary molding resin interface tends to occur due to a boss part separation resistance and it is not possible to obtain an endoscope distal end frame with high quality of appearance.

As described above, in the endoscope distal end frame 10 according to the embodiment, the diameter of the through hole 23 of the holder 20 that is the primary molding constituting the treatment tool channel is set larger than the diameter of the through hole 33 of the distal end part 30 that is the secondary molding. Accordingly, because the secondary molding resin r2 constituting the distal end part 30 passes in a molten state above the surface of the holder 20 and the holder 20 is caused to be molten again at the end of the primary and secondary molding resin interface in the through hole and is sufficiently welded with the distal end part 30, it is possible to obtain the endoscope distal end frame 10 that makes it possible to inhibit separation at the resin interface and obtain the endoscope distal end frame 10 that is excellent in appearance quality.

According to the disclosure, it is possible to prevent interfacial separation at a resin interface when a large shear stress or a tensile stress is applied to a primary and secondary molding resin interface in a through hole of an endoscope distal end frame.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general concept as defined by the appended claims and their equivalents.

What is claimed is:

1. An endoscope distal end frame comprising a double molding formed in a double molding die, the endoscope distal end frame comprising:
   a holder including a first through hole, the holder being a primary molding from among moldings formed in the double molding die, and the holder being made of a colored resin; and
   a distal end part including a second through hole that is concentric with the first through hole, the distal end part being a secondary molding from among the moldings formed in the double molding die, and the distal end part being made of a transparent resin and layered on the holder,
   wherein a diameter of the first through hole is larger than a diameter of the second through hole, thereby preventing separation at a resin interface between the first through hole and the second through hole.

2. The endoscope distal end frame according to claim 1, wherein the distal end part includes a cover configured to cover at least a part of an outer circumference of the holder.

3. The endoscope distal end frame according to claim 1, wherein the first through hole and the second through hole are holes for attaching a channel tube.

4. The endoscope distal end frame according to claim 3, wherein a step between the first through hole and the second through hole is a surface on which the channel tube abuts.

5. An endoscope comprising the endoscope distal end frame according to claim 1.

6. A method of manufacturing the endoscope distal end frame according to claim 1, the method comprising:
   providing the double molding die;
   forming the holder by injecting the colored resin into the double molding die in a primary molding process; and
   after the primary molding process, forming the distal end part by injecting the transparent resin into the double molding die in a secondary molding process.

* * * * *